United States Patent [19]

Seto et al.

[11] Patent Number: 4,707,439

[45] Date of Patent: Nov. 17, 1987

[54] SCREENING TEST FOR REVERSE-TRANSCRIPTASE CONTAINING VIRUS SUCH AS NON-A, NON-B HEPATITIS, NANBH

[75] Inventors: Belinda P. Seto; William G. Coleman, Jr., both of Bethesda; Robert J. Gerety, Potomac, all of Md.

[73] Assignee: The United States of America as represented by the Department of Health and Human Services, Washington, D.C.

[21] Appl. No.: 665,400

[22] Filed: Oct. 26, 1984

[51] Int. Cl.[4] .......................... C12Q 1/00; C12Q 1/70
[52] U.S. Cl. ............................................ 435/5; 424/3; 435/4; 435/6; 436/820; 935/76
[58] Field of Search ...................... 435/5, 7, 810, 4, 6; 436/820; 935/76

[56] References Cited

U.S. PATENT DOCUMENTS

| | | | |
|---|---|---|---|
| 4,446,237 | 5/1984 | Berninger | 435/5 X |
| 4,464,474 | 8/1984 | Coursdget | 436/820 X |
| 4,515,890 | 5/1985 | Manderino | 435/7 |
| 4,520,113 | 5/1985 | Gallo | 435/7 X |
| 4,556,643 | 12/1985 | Paau | 435/7 X |

OTHER PUBLICATIONS

Sarngadharan, M. G. et al., Methods Cancer Res., 1976, 12, 3.
Chemical Abstracts I, 98: 105631h (1983).
Chemical Abstracts II, 100: 21478k (1984).
Leong, J. C. et al., Biochim et Biophysica Acta, 782, 441-445 (Sep. 10, 1984).
Gallo, R. C. et al., Science, 220, 865-867 (1983).

*Primary Examiner*—Sidney Marantz
*Attorney, Agent, or Firm*—Holman & Stern

[57] ABSTRACT

The present invention discloses a screening test for detecting the presence of contaminating or infectious agents causing non-A, non-B hepatitis or AIDS in a blood donor setting. A kit for the detection of contaminating agents belonging to the group of retroviruses is also disclosed. Screening blood or blood related products so as to prevent spreading of infection or contamination due to retroviruses is now made possible by the present invention.

8 Claims, 1 Drawing Figure

SCREENING TEST FOR REVERSE-TRANSCRIPTASE CONTAINING VIRUS SUCH AS NON-A, NON-B HEPATITIS, NANBH

BACKGROUND OF THE INVENTION

1. Technical Field:

The present invention relates to a screening test for detecting the presence of reverse-transcriptase containing virus in blood, blood products or in any source containing such virus. More particularly, the present invention relates to the detection and diagnosis of non-A, non-B hepatitis in blood donors by determining the presence of reverse transcriptase activity in the body fluid, preferably in a blood bank setting. An advantage of the present invention is to prevent transmission of retrovirus related infection through blood donor (transfusion) program or through plasma-related products by identifying such blood, serum, plasma or products derived therefrom which may be carriers of the retrovirus by using the test disclosed herein.

2. Prior Art

Non-A, non-B hepatitis is presumed to be caused by an agent(s) which is serologically distinct from hepatitis A virus and hepatitis B virus. The diagnosis of this disease relies on the serological exclusion of hepatitis A, hepatitis B, cytomegalovirus, and Epstein-Barr virus.

Non-A, non-B hepatitis infection has been reported worldwide. It accounts for 20% of sporadic cases of hepatitis among adults. In the United States, this type of hepatitis accounts for 90% of post-transfusion hepatitis. An alarming 50% of these cases develop chronic hepatitis, and such individuals remain as potential sources of infection.

The existence of a transmissible agent in this disease has been demonstrated. However, presently there is no test to identify the non-A, non-B agent(s). The present invention for the first time demonstrates that non-A, non-B hepatitis is caused by a retrovirus or retrovirus-like agent and provides a method of screening for the same in a clinical setting, particularly in a blood-bank type program.

SUMMARY OF THE INVENTION

It is, therefore, an object of the present invention to provide a method for screening blood or blood donors capable of transmitting retrovirus related infection which may be pathogenic.

It is a further object of the present invention to provide a method of detecting in the blood, serum, plasma or plasma derived products, the presence of virus having reverse transcriptase activity.

It is another object of the present invention to provide a method of detecting the presence of an agent causing non-A, non-B hepatitis.

It is a still further object of the present invention to provide a kit for the detection of pathogenic or contagious retrovirus, including an agent causing non-A, non-B hepatitis regardless of its epidemiology.

Other objects and advantages will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
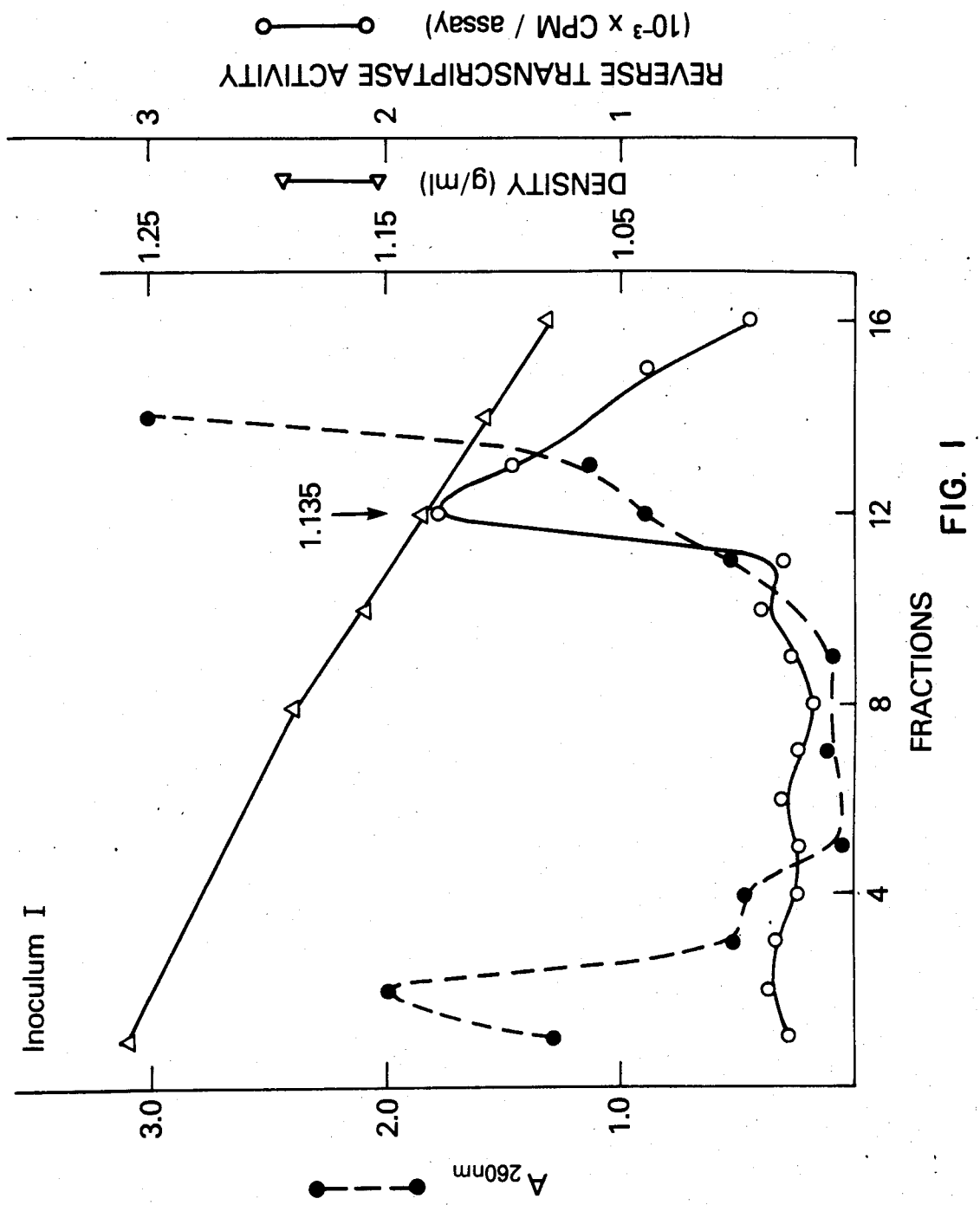
FIG. 1 shows sucrose density gradient banding of inoculum I and localization of reverse transcriptase activity.

These and other objects and advantages of the present invention are achieved by a screening test for detecting the presence of reverse transcriptase containing viruses in serum or blood, particularly in a blood donor program.

The term "blood" as used herein includes not only blood per se but also serum, plasma and any other products or fractions obtained or derived from blood or blood component.

Although the screening test described herein detects the presence of reverse transcriptase of whatsoever origin, it should be noted that the reverse transcriptase (RT) in the retroviruses as described herein are particle-associated, i.e., the RT is found encapsulated within the virus.

Hence, in order to detect the RT, a first essential step is to isolate the virus particles from soluble fraction of the blood. The isolated virus particles are then disrupted or lysed to release the RT therefrom and the specific enzyme activity then assayed.

It should be clear, therefore, that the RT referred herein is specifically of viral origin and not a soluble protein associated with normal parts of the body, tissue or body fluid.

As far as it is known, RT is found associated with all retroviruses tested. Hence, in this sense it may be designated a marker of such viruses. In particular, however, the viruses which belong to this group and which are clinically more significant are the human T-cell lymphocytotropic type I, II and III (HTLV I, II or III) and non-A, non-B hepatitis virus. It may be noted that the present invention is the first to show that non-A, non-B hepatitis is of retroviral origin; hence detectable by RT assay.

It is noted that the term "retrovirus" as used herein includes retrovirus-like agents or entities which have the same density and exhibit RT activity as found in retroviruses mentioned atove.

Although any suitable method of detecting RT activity can be used for the practice of this invention, it may be noted that the preferred methods include any radiolabelled, enzymatic, histologic, radioimmuno, fluorescent, antigenantibody, ELISA (enzyme-linked-immunosorbent assay) and the like. Monoclonal or polyclonal antibodies against purified RT or cleavage products of RT are particularly preferred. Such assay techniques are well known and should be obvious to those of ordinary skill in the art. All references or publications cited hereunder are incorporated herein by reference. Preferred methods and materials are now described.

The abbreviations used herein are as follows: NANBH, non-A, non-B hepatitis; RT, reverse transcriptase; ALT, alanine aminotransferase; AST, aspartate aminotransferase; PEG, polyethylene glycol 6000; HAV, hepatitis A virus; HBV, hepatitis B virus; RSV, Rous sarcoma virus; CMV, cytomegalovirus; EBV, Epstein-Barr virus; HTLV III, human T-cell lymphocytotropic virus, type III; AIDS, Acquired Immune Deficiency Syndrome.

MATERIALS AND METHODS

Infectious Sera and Plasma-Derived Products

Four serum inocula and two plasma-derived products were studied. Each of them had previously been shown to transmit NANBH to humans and/or to chimpanzees and to be free of HAV, HBV, CMV, and EBV.

Four inocula were sera from patients with NANBH. Inculum I was a well-defined serum obtained from a patient with chronic NANBH acquired following blood transfusion. The inoculum was known to have transmitted NANBH to another human by accidental inoculation and to chimpanzees. Inocula SE and RP are sera obtained during the acute phase of NANBH from two patients who both developed chronic NANBH. Inoculum SE is from a patient with blood transfusion-associated NANBH, and inoculum RP is from a male homosexual. Each of these sera transmitted NANBH to chimpanzees which are valid human surrogates for testing purposes. The fourth inoculum (inoculum H) was a well-defined serum obtained from a patient with chronic NANBH which was shown to transmit NANBH to chimpanzees.

Two inocula were plasma-derived products manufactured in the U.S., antihemophilic factor and fibrinogen, respectively. Each of them had been implicated in the transmission of NANBH to patients, and both were shown to transmit NANBH to chimpanzees.

NANBH Patients and Health Controls

Serum specimens from 12 patients, each with clinically, histologically, and (by exclusion) serologically confirmed NANBH were studied. These patients included recipients of blood transfusion (3 patients, all of whom developed chronic NANBH), intravenous drug users (4 patients, 3 of whom developed chronic NANBH), and sporadic cases without any known exposure to hepatitis agents (5 patients, 2 of whom developed chronic NANBH). The diagnosis of NANBH was made in each of these patients based upon serum ALT activity (at least 5 times the upper limit of normal, 40 IU/ml), liver histology consistent with viral hepatitis and the absence of serologic markers for HAV (anti-HAV antibodies of the IgM-type), HBV (HBsAg in serum or anti-HBc alone in serum), CMV, or EBV.

Control sera were obtained from 49 healthy individuals, of whom 13 were workers in a plasma derivatives research and regulatory laboratory and 36 were paid plasmapheresis donors. Both of these groups are known to be at somewhat higher risk of NANBH than the general population.

Chimpanzees

Two chimpanzees (*Pan troglodytes*), 1278 and 1284, were obtained from a breeding colony as described by Tabor et al in Lancet, 1978, 1, 463 and Tabor et al in N. Engl. J. Med, 1980, 303, 140.

Detection of Reverse Transcriptase (RT) Activity

RT Assay. Serum samples (100 µl), negative control material (fetal bovine serum), and positive control material (Rouse sarcoma virus, $1 \times 10^{10}$ particles) were all initially centrifuged in 5 ml of 35% glycerol in 0.5 M Tris-HCl, pH 7.0, at 77,000 ×g for 1 hour at 4° C. to pellet viral particles from serum proteins as described by Sarngadharan et al in Methods Cancer Res., 1976, 12, 3. The pellet was treated with 0.25% octylphenol ethylene, oxide condensate (Nonidet P40) to disrupt viral particles. Each treated sample was then added to 40 µl of solution consisting of 60 mM Tris-HCl, pH 8.3, 8 mM MgCl, 80 mM KCl, 20 mM dithiothreitol, 0.1 µg actinomycin D, 80 µM each of unlabeled deoxyribonucleoside triphosphate, 20 µM [$^3$H]TTP (thymidine triphosphate, specific activity 1.2 Ci/mmol), and 1 µg poly(rA) p(dT)$_{10}$ as template-primer. The reaction was incubated at 37° C. for 1 hour and terminated by adding 40 µl of 1 mg/ml yeast tRNA and 5 ml 10% TCA containing 0.2 mM sodium phrophosphate. After 30 minutes, the precipitable radioactivity was collected on glass fiber filters, dried, and the radioactivity determined by liquid scintillation. The sample was considered positive if the sample cpm were 2 times the negative control cpm (mean $0.35 \times 10^3$). This positive cut-off ($0.7 \times 10^3$ cpm), based on a titration of RSV particles, represents the RT activity associated with $1 \times 10^4$ particles of RSV. A gross estimate of virus titer in a given inoculum can, therefore, be obtained by relating the RT activity in cpm associated with various numbers of RSV particles, and comparing the cpm obtained with those for the inoculum. The product assayed is the radiolabelled DNA.

Localization of RT in Sucrose Gradient Ultracentrifugation Fractions of Infectious Sera One ml each of inoculum I and inoculum SE were centrifuged separately in an SW41 rotor by layering on 11 ml of a 10% to 60% (by weight) sucrose gradient made in 10 mM Tris-HCl, pH 7.5, 100 mM NaCl, and 1 mM EDTA, and centrifuged at 30,000 rpm for 19 hours at 4° C. in a Beckman LB-70 ultracentrifuge. Fractions (0.7 ml each) were collected from the bottom of the gradient and the absorbance at 260 nm determined with an LKB UVcord. After removal of sucrose by centrifugation, the fractions were assayed for RT activity as described.

Inoculation of RT Positive Ultracentrifugation Fractions into Chimpanzees

Fractions from each individual gradient which contained RT activity were pooled (fractions 12-15 in 2.8 ml), filter-sterilized (0.22 µM filter), and injected intravenously into chimpanzees 1278 (inoculum I) and 1280 (inoculum SE). Both chimpanzees were bled weekly to monitor serum enzyme activities (ALT and AST) and serological markers of hepatitis. In addition, liver biopsies were obtained biweekly and examined by light microscopy for evidence of hepatitis and by electron microscopy for specific ultrastructural changes in NANBH.

Biophysical and Biochemical Characterization of RT

In three serum specimens (inocula I, SE, and RP), the RT activity was assayed following treatment with 6.5% polyethylene glycol 6000 (PEG) according to Welsh et al in Nucleic Acids Res., 1980, 8, 2349 and, in a separate analysis, in the presence of 5 µg RNAse A and two different exogenous template-primers as described by Goodman, et al in Proc. Natl. Acad. Sci. U.S.A., 1971, 68, 2203 and Milstein, et al in J. Clin. Microbiology, 1975, 1, 353.

RESULTS

Particle-associated RT activity was detected in all 6 infectious NANBH materials and in all 12 sera from patients with acute or chronic NANBH. The RT activity ranged from $0.85 \times 10^3$ cpm to $16.6 \times 10^3$ cpm. In contrast, 47 of 49 sera (96%) from healthy controls lacked enzyme activity (CPM ranged from $0.2 \times 10^3$ to $0.56 \times 10^3$). Sera from two healthy controls yielded $1.2 \times 10^3$ and $1.0 \times 10^3$ cpm, respectively, and were regarded as low positives (cut-off $0.7 \times 10^3$ cpm). Table I shows the data from these studies.

TABLE I

REVERSE TRANSCRIPTASE (RT) ACTIVITY

| Material studied | No. tested | No. positive (%) | RT activity ($\times 10^3$ cpm) (range and mean) |
|---|---|---|---|
| Sera proven infectious in previous NANBH studies | 4 | 4 (100%) | $1.40^a$–16.6 mean: 5.95 |
| Plasma-derived products proven infectious in previous NANBH studies | 2 | 2 (100%) | 0.85–1.30 mean: 1.08 |
| Serum samples from NANBH patients obtained during the acute phase of infection | 12 | 12 (100%) | 0.86–2.70 mean: 1.49 |
| Serum samples from healthy laboratory workes and paid plasmapheresis donors | 49 | 2 (4%) | $1.0$–$1.20^b$ mean: 1.1 |

$^a$This value represents the RT activity in 100 μl of a $10^{-4}$ dilution of inoculum H.
$^b$These values represent the RT activity in the two positive samples. The negative samples have values ranging from $0.21 \times 10^3$ to $0.56 \times 10^3$ cpm.

As shown in FIG. 1 peak RT activity for inoculum I banded at 1.14 g/ml in a sucrose gradient. Similar banding patterns were obtained with two other serum inocula. Peak RT activity for inocula SE and RP are also banded at 1.14 g/ml.

Following inoculation of chimpanzees with RT-positive sucrose gradient fractions from either inoculum I (chimpanzee 1278) or inoculum SE (chimpanzee 1284), both animals developed NANBH as confirmed by elevations of serum ALT activity (at least 3 times the baseline level), histologic evidence of hepatitis by light microscopy, and specific ultrastructural cytoplasmic alterations (type C-III tubules) by electron microscopy.

The biophysical and biochemical characteristics of the RT activity detected by the assay desribed here appear in Table II.

TABLE II

NATURE OF THE REVERSE TRANSCRIPTASE (RT) ACTIVITY

| Addition$^b$ or Treatment | RT activity ($\times 10^3$ cpm/assay) |
|---|---|
| Complete$^a$ | 4.09 |
| Actinimycin D, 100μg | 4.01 |
| 6.5% PEG pellet$^c$ | 4.11 |
| poly(rA).p(dT)$_{10}$, 1 μg | 7.29 |
| poly(dA).p(dT)$_{10}$, 1 μg | 3.64 |
| poly(rA).p(dT)$_{10}$, 1 μg, and RNAse A, 5 μg | 4.34 |

$^a$The complete system represents the sandard RT reaction described in Materials and Methods with the exception of the exogenous template. The activity represents synthesis using the endogenous template only.
$^b$Addition to the complete reaction described above.
$^c$PEG precipitation of viral particles prior to addition to complete system.

Besides banding at a discrete density, RT activity is associated with viral particles since it was completely recovered in the 6.5% PEG precipitate. The RT activity showed a preference for poly(rA) p(dT)$_{10}$ over poly(dA) p(dT)$_{10}$ as template-primer, a feature which distinguishes the viral enzyme from cellular DNA polymerases. Additionally, the incorporation of [$^3$H]TTP was insensitive to actinomycin D, which inhibits DNA-dependent DNA synthesis. The viral RT activity with endogenous template-primer was sensitive to RNAse A digestion, whereas the reaction with exogenous template-primer, [poly(rA) p(dT)$_{10}$]was unaffected.

The finding of particle-associated RT activity in 4 infectious sera and in 2 infectious plasma-derived products, as well as in 12 serum samples from the acute or chronic phase of NANBH, demonstrated that this disease is caused by a virus or a virus-like agent possessing this enzyme. The location of this RT activity in sucrose gradient fractions (peak activity at 1.14 g/ml) and the transmission of typical NANBH to chimpanzees by inoculating RT-positive sucrose gradient fractions provide evidence that the NANBH agent in the sera and plasma-derived products studied (as well as in the patient sera examined) is a retrovirus or retrovirus-like agent(s). The finding of RT activity in the sera of 2 out of 49 controls which banded at a density consistent with that of retrovirus strongly suggested that these individuals are infected with a retrovirus or retrovirus-like agent. Indeed, all 49 of the controls were at a higher risk for NANBH than the general population.

The finding of RT activity in all 12 sera from patients with different epidemiological types of NANBH indicated that one or more retrovirus or retrovirus-like agent(s) caused all 12 cases of NANBH. The absence of RT activity in 47 of 49 sera from healthy laboratory workers and paid plasma donors, all of whom are at a higher risk for acquiring NANBH than the general population, support the specificity of the RT assay employed here. Additional evidence for this specificity is the preference shown for poly(rA) p(dt)$_{10}$ as template-primer, the precipitation of RT by PEG, the susceptibility of the endogenous template to inactivation by RNAse A, resistance of the reaction product to alkali hydrolysis, and the localization of the RT activity and infectivity in sucrose gradients at a density consistent with that reported for retrovirus as cited in Sarngadharan, et al, supra.

Known characteristics of NANBH and of the agent(s) causing this disease appear to be consistent with the etiology being a retrovirus or retrovirus-like agent. Inactivation of NANBH agents has been accomplished by formalin, heat, or chloroform, also consistent with their being retroviruses. Chronic infections are common following infection with the NANBH agent(s), especially those acquired via blood transfusion. Retroviruses characteristically cause chronic infections. Antigen-antibody systems described in association with NANBH are consistent with the development of antibodies to both the external and internal antigens of retroviruses, all of which appear to coexist with infectious virus in serum. At least one antigen detected by counterelectrophoresis and purified from inoculum I appears to be a glyco-protein similar to one described by Schupbach et al in Science 1984, 224, 503, and present on the surface of the HTLV III retrovirus.

Specific cytoplasmic ultrastructural changes have been consistently seen during NANBH in chimpanzees. Similar alterations have been reported in the lymphocytes of patients with the Acquired Immune Deficiency Syndrome (AIDS), a syndrome which is associated with chronic infection with the retrovirus HTLV III as described by Schaff et al in Lancet 1983, 1, 1336.

Additionally, a known amount of human T-cell lymphocytotropic virus, Type III (HTLV III) when added to human plasma was detected by reverse transcriptase activity. Three products derived from plasma containing HTLV III, anti-hemophilic factor concentrate, fibrinogen and plasma-protein fraction were also found to contain reverse transcriptase activity. Reverse transcriptase activity was directly related to virus titer, indicating the utility of using reverse transcriptase activity to estimate the HTLV-III virus titer in plasma.

It is clear from the above that the present invention now makes it possible for blood banks and producers of blood related products to screen all blood donors and blood products and identify those capable of transmitting retrovirus related pathogenic conditions including NANBH and AIDS. A single screening test utilizing the present invention enables the detection, diagnosis and elimination of retrovirus related contagious or infectious conditions.

A kit comprising a container containing a suitable RT assay system selected from the group consisting of an enzymatic assay, an antigen-antibody titer assay including mono- or polyclonal antibodies and the like would be most valuable for clinical and laboratory use in accordance with the present disclosure. Such accessories as micro-titer plates, radiolabelled substrates, pipettes, buffers, coenzymes and the like which are routinely common and well known in the art are included in the kit in accordance with the present invention.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for screening a blood composition for the presence of retrovirus particles associated with non-A, non-B hepatitis comprising:
   (a) isolating said retrovirus particles from a sample of blood composition;
   (b) disrupting or lysing the isolated retrovirus particles to thereby release the reverse transcriptase therefrom;
   (c) assaying the reverse transcriptase activity;
   (d) comparing the activity assayed in step (c) with that assayed in a similarly treated control sample; and
   (e) concluding the presence of retrovirus particles associated with non-A, non-B hepatitis in said blood composition when the reverse transcriptase activity in the blood composition is about twice or more than that in the control.

2. The method of claim 1 wherein the blood composition to be screened is serum, plasma or a fraction or product derived from plasma or serum.

3. The method of claim 1 wherein the assaying of step (c) is carried out histologically or immunochemically.

4. A method of preventing transmission between living subjects of a non-A, non-B hepatitis infection comprising identifying a blood composition from one subject as having retrovirus particles associated with non-A, non-B hepatitis by the method of claim 1 and isolating the blood composition or individual so infected from living subjects.

5. A method for screening a blood composition for the presence of retrovirus particles comprising:
   (a) isolating said retrovirus particles from a sample of blood composition;
   (b) disrupting or lysing the isolated retrovirus particles to thereby release the reverse transcriptase therefrom;
   (c) assaying the reverse transcriptase activity;
   (d) comparing the activity assayed in step (c) with that assayed in a similarly treated control sample; and
   (e) concluding the presence of retrovirus particles in said blood composition when the reverse transcriptase activity in the blood composition is about twice or more than that in the control.

6. The method of claim 5 wherein the blood composition to be screened is serum, plasma or a fraction or product derived from plasma or serum.

7. The method of claim 5 wherein the assaying of step (c) is carried out histologically or immunochemically.

8. A method of preventing transmission between living subjects of a retrovirus infection comprising identifying a blood composition from one subject as having retrovirus particles by the method of claim 5 and isolating the blood composition or individual so infected from living subjects.

* * * * *